US011195623B2

(12) United States Patent
Choi et al.

(10) Patent No.: US 11,195,623 B2
(45) Date of Patent: Dec. 7, 2021

(54) METHOD FOR DENTAL IMPLANT PLANNING, APPARATUS FOR SAME, AND RECORDING MEDIUM HAVING SAME RECORDED THEREON

(71) Applicant: OSSTEMIMPLANT CO., LTD., Seoul (KR)

(72) Inventors: Kyoo Ok Choi, Seoul (KR); Tae Hwan Kim, Seoul (KR); Seung Yong Hwang, Seoul (KR); Seong Yun Lee, Bucheon-si (KR)

(73) Assignee: OSSTEMIMPLANT CO., LTD., Seoul (KR)

( * ) Notice: Subject to any disclaimer, the term of this patent is extended or adjusted under 35 U.S.C. 154(b) by 307 days.

(21) Appl. No.: 15/541,204

(22) PCT Filed: Dec. 4, 2015

(86) PCT No.: PCT/KR2015/013260
§ 371 (c)(1),
(2) Date: Jun. 30, 2017

(87) PCT Pub. No.: WO2016/108454
PCT Pub. Date: Jul. 7, 2016

(65) Prior Publication Data
US 2017/0364659 A1      Dec. 21, 2017

(30) Foreign Application Priority Data

Dec. 31, 2014   (KR) ................. 10-2014-0195209
May 15, 2015   (KR) ................. 10-2015-0067951

(51) Int. Cl.
*G06F 30/20*      (2020.01)
*A61C 13/00*     (2006.01)
(Continued)

(52) U.S. Cl.
CPC ............... *G16H 50/50* (2018.01); *A61C 8/00* (2013.01); *A61C 13/0004* (2013.01); *A61C 19/04* (2013.01); *G06F 30/20* (2020.01)

(58) Field of Classification Search
CPC ......... G16H 50/50; G06F 30/20; A61C 19/04; A61C 8/00; A61C 13/0004
See application file for complete search history.

(56) References Cited

U.S. PATENT DOCUMENTS

| 4,504,230 A | * | 3/1985 | Patch | ............... A61C 3/00 433/219 |
| 2010/0119992 A1 | * | 5/2010 | Satoh | ............ A61C 13/097 433/167 |

(Continued)

FOREIGN PATENT DOCUMENTS

| CN | 102084365 A | 6/2011 |
| CN | 102159155 A | 8/2011 |

(Continued)

OTHER PUBLICATIONS

Extended European Search Report for European Application No. 15875548, dated Sep. 3, 2018.
(Continued)

*Primary Examiner* — Omar F Fernandez Rivas
*Assistant Examiner* — Michael Edward Cocchi
(74) *Attorney, Agent, or Firm* — Novick, Kim & Lee, PLLC; Jae Youn Kim; Jihun Kim

(57) ABSTRACT

The present invention relates to a method of dental implant treatment planning, a device and a recording medium therefore. The device for dental implant treatment planning according to the present invention can move or rotate the grouped objects together in 2D or 3D model about teeth arrangement for implant treatment planning with grouping function of the implant objects. So, it decreases complexity of manipulation of the implant objects, provides users with (Continued)

convenience to easily modify position or size of the implant objects, and improves the accuracy of the modification.

11 Claims, 8 Drawing Sheets

(51) Int. Cl.
    *G16H 50/50*     (2018.01)
    *A61C 19/04*     (2006.01)
    *A61C 8/00*     (2006.01)

(56) References Cited

U.S. PATENT DOCUMENTS

| | | | | |
|---|---|---|---|---|
| 2010/0151417 | A1* | 6/2010 | Nilsson | A61C 13/0004 433/167 |
| 2010/0311028 | A1* | 12/2010 | Bell, III | G09B 23/28 434/263 |
| 2011/0224955 | A1* | 9/2011 | Fisker | G06F 30/00 703/1 |
| 2012/0015316 | A1 | 1/2012 | Sachdeva et al. | |
| 2012/0070803 | A1* | 3/2012 | Manai | G16H 50/50 433/213 |
| 2012/0197620 | A1* | 8/2012 | Gao | G16H 50/50 703/11 |
| 2012/0239364 | A1* | 9/2012 | Glor | A61C 1/084 703/11 |
| 2013/0066598 | A1* | 3/2013 | Fisker | A61C 19/05 703/1 |
| 2013/0158694 | A1* | 6/2013 | Rubbert | G06F 30/00 700/98 |
| 2014/0257763 | A1* | 9/2014 | Fang | A61C 13/0004 703/1 |
| 2015/0056576 | A1* | 2/2015 | Nikolskiy | A61C 9/004 433/214 |

FOREIGN PATENT DOCUMENTS

| | | |
|---|---|---|
| CN | 102438545 A | 5/2012 |
| CN | 103108604 A | 5/2013 |
| CN | 104125814 A | 10/2014 |
| KR | 10-2005-0082526 | 8/2005 |
| KR | 10-2010-0126700 | 12/2010 |
| KR | 10-2011-0074186 | 6/2011 |
| KR | 10-2012-0131063 | 12/2012 |
| KR | 10-2013-0097216 | 9/2013 |
| KR | 10-2014-0113971 | 9/2014 |
| WO | 2013/053903 | 4/2013 |

OTHER PUBLICATIONS

International Search Report for International Application No. PCT/KR2015/013260, dated Mar. 7, 2016.

* cited by examiner

METHOD FOR DENTAL IMPLANT PLANNING, APPARATUS FOR SAME, AND RECORDING MEDIUM HAVING SAME RECORDED THEREON

FIELD

The present invention relates to a method of dental implant treatment planning, a device and a recording medium therefore. More specifically, the present invention relates to a technology that reduces complexity and improves accuracy for determining a position of implant objects when planning a dental implant treatment.

BACKGROUND OF INVENTION

The dental implant treatment goes through an implant treatment planning prior to the treatment to determine appropriate variables of the implant to the patient's bone condition, such as size, type, position, orientation and shape, etc.

First of all, the implant treatment planning acquires images such as X-ray, CT, MRI, panorama, etc. to examine quantity and quality etc. of both jaw and dental bone of a patient through image acquisition equipment, and simulates position, orientation, and form, etc. through a software program by choosing type, size, etc. of the implant which fits the patient's condition.

The existing software program for dental implant planning is implemented to generate each object of the implant such as a fixture, an abutment, a sleeve, a virtual crown and modify position or size of the respective object. Not only is it quite cumbersome to generate and modify position or size of the respective object, but also there is a problem that considerable time and effort are spent due to re-modification of another object which is needed by the modification of the initial object.

Due to these sorts of cumbersome and time consuming issues, a software program for implant treatment planning becomes more inconvenient to users.

In addition, as a means to evaluate the occlusion, it is to be simulated by generating an object like a virtual crown or using wax-up etc. made by some equipment like a scanner. According to the conventional method of dental implant treatment planning, the size of a virtual crown size cannot be modified and although modification function is given, it only provides limited function to increase or decrease the size of the virtual crown in all directions with the same ratio, wherein the virtual crown has the same weight of the size modification in the left and right direction from the center axis of the virtual crown.

Due to this, it has been hard to establish the implant treatment plan which reflects the occlusion with natural teeth.

DETAILED DESCRIPTION OF THE INVENTION

Technical Challenge

An object of the present invention, which is to solve aforementioned problems, is to provide a method for a dental implant treatment planning to decrease the complexity of the object manipulation and to provide users with convenience by grouping the implant objects and modifying the position of all the objects that belong to same group simultaneously with an object manipulation, and a device and a computer-readable recording medium therefore.

In addition, another object of the present invention is to provide a method for a dental implant treatment planning to decrease the complexity of the object manipulation and to provide users with convenience by setting a limit range of the objects based on occlusion evaluation, modifying the size within the limit range, and moving positions of all the objects that belong to the same group with the virtual crown simultaneously when the center of the virtual crown is changed due to the size modification, and a device and a computer-readable recording medium therefore.

Furthermore, another object of the present invention is to provide users with convenience for modifying manipulation by providing information in case objects are out of the limit range when users modify a position or size of objects.

The Solution of Invention

In order to achieve one or more of the above objects, the method of dental implant treatment planning according to one aspect of the present invention comprises: generating a multi-dimensional image model corresponding to specific teeth arrangement; placing in the image model at least one object that forms the implant; grouping multiple objects among the implant placed in the image model; and moving the position of the grouped objects together when one of the grouped objects is moved or rotated.

Herein, the object that forms the implant comprises a virtual crown and a fixture, and the method comprises moving the position of the fixture along with the virtual crown if center of the virtual crown changes according to the size modification of the virtual crown when modifying size of the virtual crown.

Also, the method may further comprise identifying natural teeth and occlusal surface corresponding to the teeth arrangement; setting up, down, left and right limit range wherein the objects can be placed on the basis of identification result, wherein the execution of at least one command among position movement, rotation and size modification of the objects is made within the limit range.

In addition, the limit range is set based on at least one among positions of maximum convexity, neural tube and alveolar bone of tooth which is adjacent to the virtual crown.

Also, setting up, down, left and right limit range comprises restricting the up and down movement of the virtual crown by identifying the occlusal surface.

The Effect of Invention

As stated above, according to embodiments of the present invention, complexity of manipulation of implant objects is decreased, users are provided with convenience to easily modify the position of objects and the accuracy of the modifying is increased.

DETAILED DESCRIPTION OF EXEMPLARY EMBODIMENTS

Hereinafter, exemplary embodiments of the present invention will be described in detail referring to the appended drawings.

Figure 1:
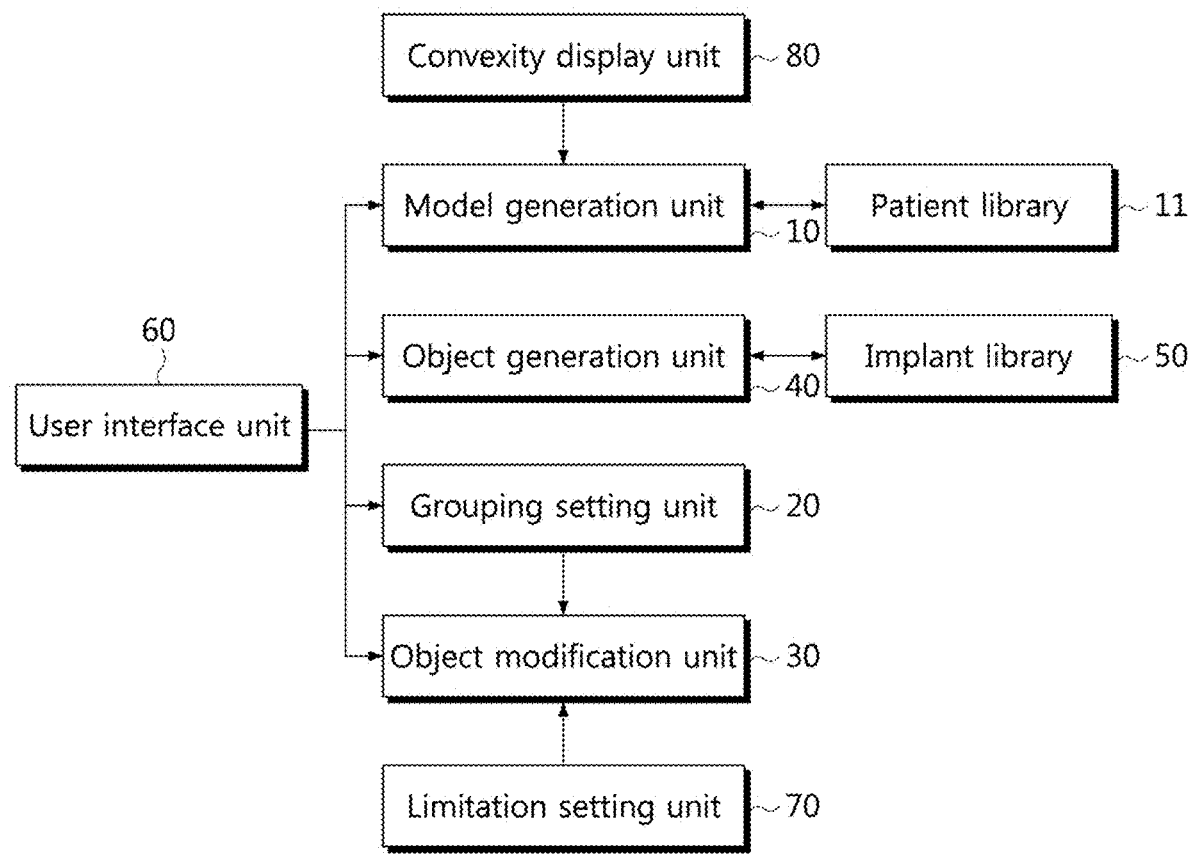
FIG. 1 is a block diagram of the device for the dental implant treatment planning according to an embodiment of the present invention.

FIG. 1 is a block diagram of the device for the dental implant treatment planning according to an embodiment of the present invention. Referring to FIG. 1, the device for the dental implant treatment planning according to the present invention comprises a model generation unit 10, a grouping setting unit 20, and an object modification unit 30.

The model generation unit 10 is to generate a multi-dimensional model about patient's teeth arrangement for the implant treatment planning, and the model for patient's teeth arrangement herein can be either 2D or 3D model.

The model for patient's teeth arrangement is generated on the basis of an image of patient's jaw or teeth and it also can be generated by matching scan prosthesis or individually digitized prosthesis with anatomical structure in X-ray, MRI, or panorama image.

Referring to FIG. 1, the device for the dental implant treatment planning according to another embodiment of the present invention comprises patient's library 11 which the image or model of patient's jaw or teeth is stored in, and a model generation unit 10 that displays the image or a model corresponding to user's selection from the patient's library 11.

The grouping setting unit 20 is to set or reset the group of the implant objects placed in patient's model, and if multiple objects are set to belong to one group, the multiple objects of the same group are processed as one thing.

Herein, the implant object means all kinds of the object that forms an implant, to comprise a virtual crown, a fixture, an abutment and a sleeve etc.

The object modification unit 30 is to modify position or size of implant objects, and it moves, rotates, modifies or changes the position of the implant object depending on a manipulation command from user. The object modification unit 30 modifies either grouped objects together or each object apart according to whether grouping of the implant objects is set or not.

In case objects are grouped, the grouping setting unit 30 makes a process of all the objects in the same group as one thing, so that relative position relationship of all the objects in the same group is maintained when moving or rotating the group. Therefore, it is needless to move the respective object and adjust the relative position relation of the implant objects, and also only one manipulation makes it possible to modify all the related objects simultaneously, which is very convenient.

Referring to FIG. 1, the device for the dental implant treatment planning according to another embodiment of the present invention can comprise an implant library 50, an object generation unit 40, and a user's interface unit 60.

The implant library 50 stores a variety of implant objects by company, type, size, or length.

The object generation unit 40 is to generate objects that form an implant. The unit 40 can get the objects from the implant library 50 according to the user selection or its selection or import the result of the Wax-up to display the objects in the image.

The user interface unit 60 is to receive user's commands, and to be implemented with mouse, keyboard, button, keypad, and/or GUI on the screen.

Figure 2:
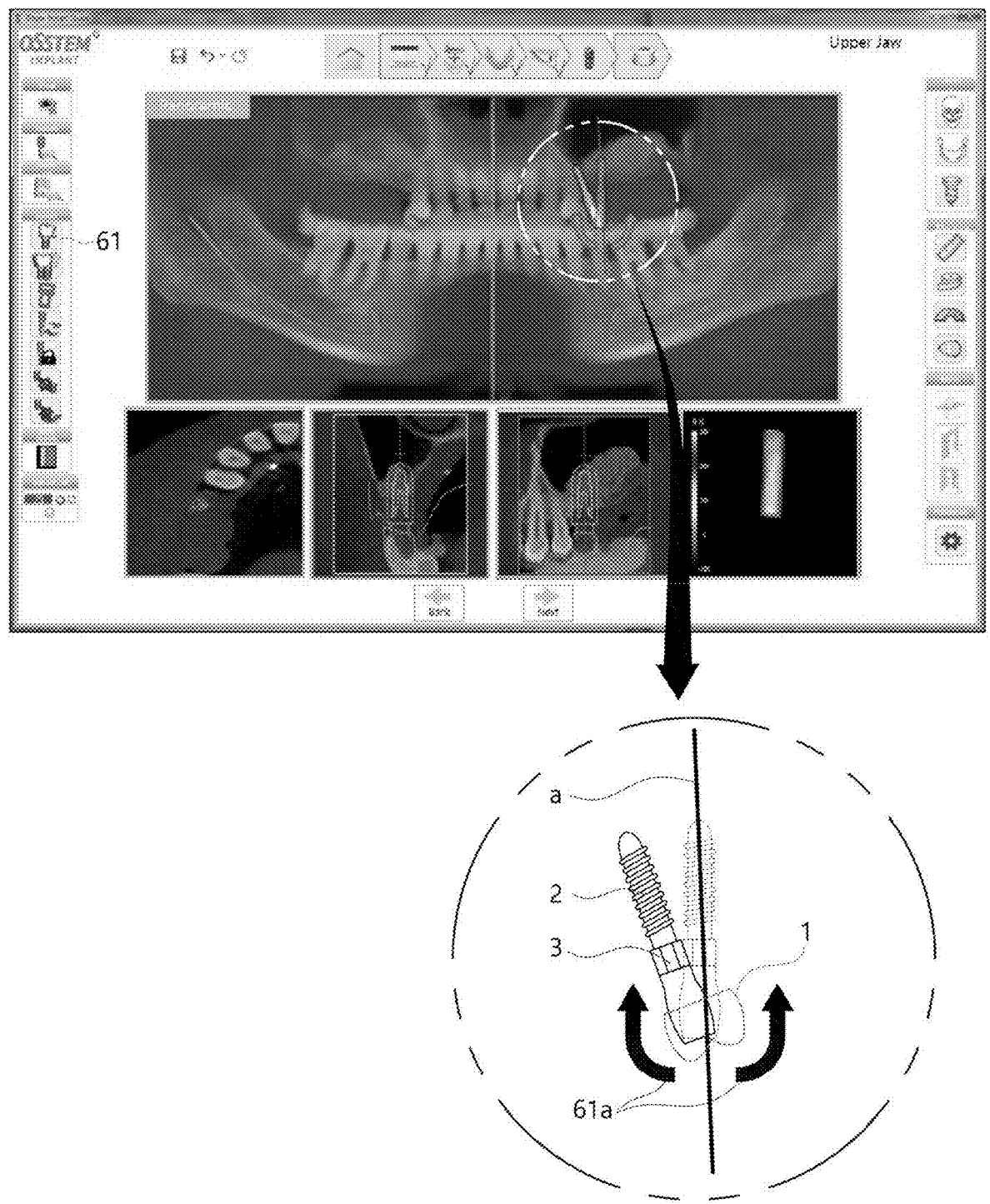
FIG. 2 illustrates an example of an implementation screen of the device for the implant treatment planning according to an embodiment of the present invention.

FIG. 2 illustrates an example of an implementation screen of the device for the implant treatment planning according to an embodiment of the present invention.

Referring to FIG. 2, the implementation screen of the device for the implant treatment planning shows the implant object on the model of patient' teeth arrangement.

The implant object comprises the virtual crown 1, fixture 2 and abutment 3. The implant objects are placed in respective position according to user's selection or input.

The implementation screen of the device for the implant treatment planning in FIG. 2 displays multiple GUI menus, and the most GUI menus illustrate as icons. In the left side of the screen of FIG. 2, there is the grouping setting menu about position movement or rotation for a virtual object.

If a user clicks the grouping setting icon 61 on the screen of FIG. 2, then its function is to be activated. And if the user clicks this icon once again, the function is to be deactivated. Activation and deactivation states are displayed with different colors, which makes the user Figure out intuitively whether an implant object is grouped or not.

Also, the implementation screen of the device for the implant treatment planning includes the menu icon 61a to move or rotate a position of the implant object. In FIG. 2, the menu icon 61a is expressed as arrow 61a around the implant object, so the user can move or rotate the implant object by clicking or dragging one end of the icon 61a.

FIG. 2 depicts the left rotation of the implant object, where the virtual crown 1 is rotated so that the other object such as the fixture 2 etc. in the same group is rotated simultaneously. In FIG. 2, points out the center axis of the virtual crown 1, and the movement of the center axis has other objects in the same group shift or rotate by the same as the movement of the center axis.

In this case, the center axis lines of implant objects do not need to coincide. In some cases, the center axis lines of implant objects can be misaligned slightly depending the patient's condition, and the implant objects will be moved or rotated with keeping the state of the misalignment of the center axis lines.

Meanwhile, the function of grouping the implant objects can be implemented to work only when moving or rotating specific objects and not to work when moving or rotating the other objects.

For example, if a movement or rotation command of the virtual crown 1 is input, all the related objects can be moved or rotated simultaneously when the grouping function is activated. On the other hand, if a movement or rotation command of the fixture 2 is input, although the grouping function is activated, only the fixture 2 can be moved or rotated and all the related objects can remain.

The above implementation example relates to a general procedure for the implant planning to determine the position of the virtual crown 1 and then to determine the position of the other objects.

In another implementation example, it is to be implemented to move or rotate the grouped objects simultaneously only in selection of the menu icon and mover or rotate the respective object in input of the other means, wherein the menu icon selected for moving same grouped objects simultaneously can be displayed when the grouping function is activated.

The above implementation example has the advantage that users select or handle easily depending on user's decision, because users can choose to modify multiple objects simultaneously or modify just one object by selecting the input icon for the command.

Meanwhile, the device for dental implant treatment planning according to another embodiment of the present invention will be described by referencing FIG. 1 and FIG. 3.

Referring to FIG. 1, the device for dental implant treatment planning according to another embodiment of the present invention can comprise the model generation unit 10, the grouping setting unit 20, and the object modification unit 30, and it can further comprise the object generation unit 40, the patient's library 11, the implant library 50 or the limitation setting unit 70. The explanation on the same or similar part with the stated embodiment is to be skipped within the overlapping range.

The device for dental implant treatment planning according to another embodiment of the present invention can perform a size modifying function for implant objects. Hereinafter, the example of size modification for a virtual crown among the implant objects will be described.

When size modification commands of a virtual crown are entered by users, the object modification unit 30 modifies the size of a virtual crown based on the boundary surface of teeth adjacent to a virtual crown.

Herein, the boundary surface for the adjacent tooth includes the boundary surface for maximum convexity of the adjacent tooth crown, and the modification unit 30 should not exceed its boundary surface when modifying size of a virtual crown.

For example, a size modification command for the virtual crown can be input by dragging or pulling an outline of the virtual crown with mouse control, and the size of virtual crown can be increased or decreased according to the amount of such a user input.

At this point, if the implant objects are grouped and the position of the virtual crown are moved by modifying size of the virtual crown, the other objects that belong to the same group with the virtual crown will move together.

However, although the implant objects are grouped, if the position of the virtual crown has not been changed, for example, if the center axis has not been changed, the positions of other objects will not be changed.

The limitation setting unit 70 is to recognize natural teeth and occlusal surface based on image analysis, and to set or reset up, down, left and right limit range where implant objects can be placed. The activation or deactivation of limitation setting function can be selected by the user interface unit 60. Meanwhile, according to another embodiment of the present invention, the limitation setting function does not be selected by the user interface unit 60, but remains always activated to limit movement, rotation, modification etc. within the limit range automatically. Hereinafter, an embodiment of the present invention will be described in an example which the limit range setting function can be either activated or deactivated by user's selection.

If the movement range limitation setting function of the limitation setting unit 70 is activated, the object modification unit 30 will do within up, down, left and right limit range when moving position, rotating or modifying size of implant objects.

Herein, the up, down, left and right limit range are set by the position of neural tube, alveolar bone, and maximum convexity of crown of teeth (e.g. natural teeth, artificial teeth or virtual teeth) adjacent to a virtual crown.

If user's modification commands are out of the up, down, left and right limit range, users are informed of this by icon or message displayed on the screen or by sound or voice output.

For example, when commanded to expand the size of a virtual crown, if size expansion is because the one side edge of the virtual crown expands to boundary surface for the maximum convexity of the adjacent teeth crown, it is executed to expand the other side edge of the virtual crown to the desired size by users. Also, if size expansion is disabled because both of the side edges expand to both adjacent teeth, users are informed of this by displayed icons for the state.

If the movement range limitation setting function of the limitation setting unit 70 is deactivated, the object modification unit 30 modifies the objects according to user's command without limits of the movement range when modifying objects.

Figure 3:
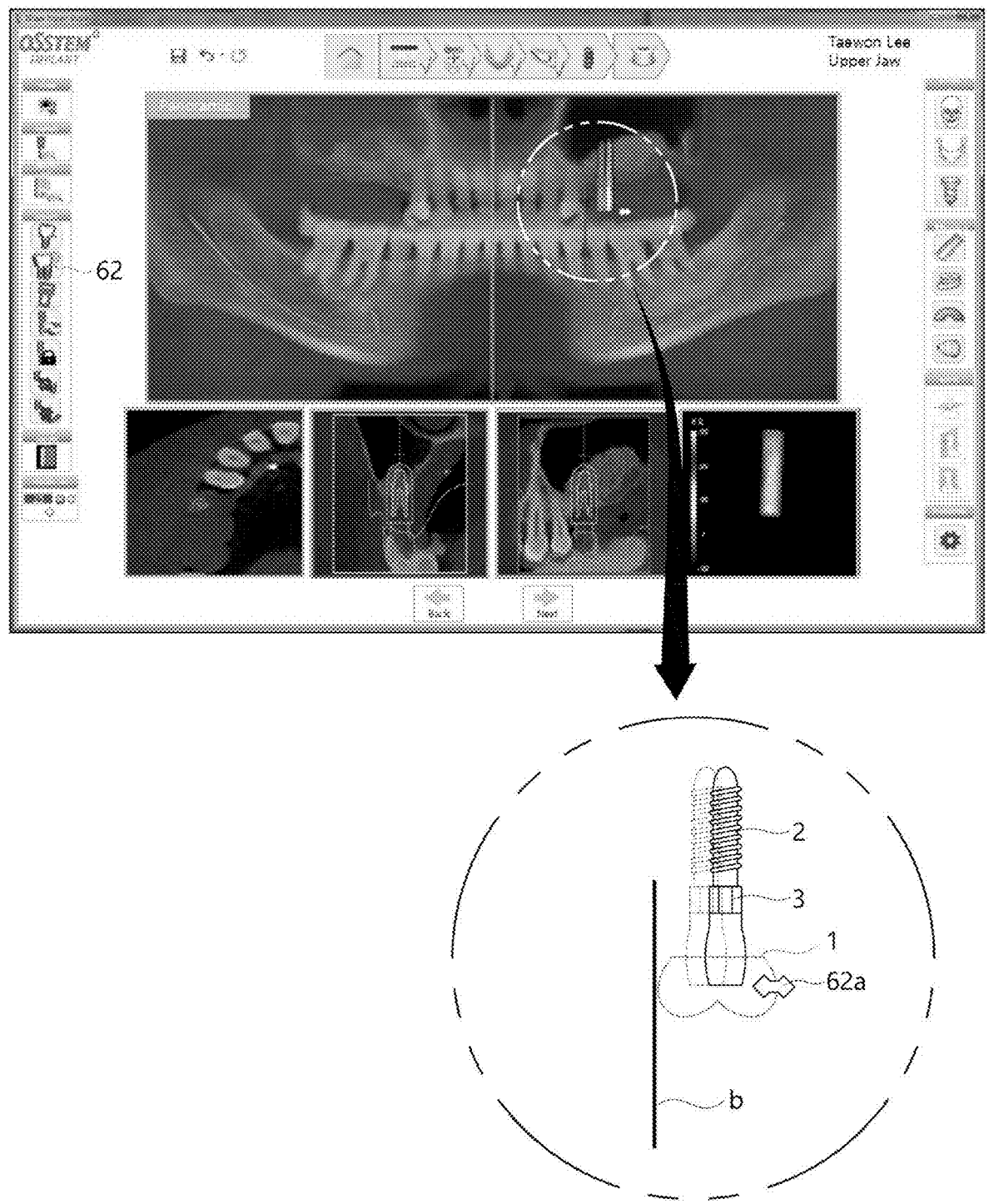
FIG. 3 illustrates an example of an implementation screen of the device for the implant treatment planning according to another embodiment of the present invention.

FIG. 3 illustrates an example of an implementation screen of the device for the implant treatment planning according to another embodiment of the present invention. Referring to FIG. 3, an implementation screen of the device for the implant treatment planning according to another embodiment of the present invention shows size modification and grouping setting menu for a virtual crown.

The screen in FIG. 3 shows the size modification or grouping setting function of a virtual crown 1 as an icon. The function is activated if clicking the icon, but it is deactivated if clicking the icon once again. Also, to express the activation and deactivation with different colors has users figure out intuitively whether the function is activated or not.

In FIG. 3, when clicking the icon 62, an icon 62a which user can adjust the size of the virtual crown 1 with, is generated around the implant objects. Users can increase or decrease it in one or both sides by clicking or dragging the icon in all directions.

In FIG. 3, b points out the boundary surface with adjacent teeth, and when the limitation setting function of the limitation setting unit 70 is activated, the expanded virtual crown is limited not to go over the boundary surface.

In FIG. 3, the user increased the virtual crown 1 by clicking or operating the icon, and the virtual crown 1 has been increased on the right side of the boundary surface of the adjacent tooth so that, as a result, it can be understood that the center of the virtual crown 1 has been changed.

At this point, if the implant objects are grouped, the other objects are to be moved together with the center axis of the virtual crown moved. In FIG. 3, it shows an example that the fixture 2 and the abutment 3 has been moved together according to the movement of the center axis of virtual crown 1.

In case of setting grouping like this, since the object modification unit 30 recognizes objects as one thing, so if the center axis is moved because the size of a virtual crown is changed, so that relative position relationship of all the objects in the same group is maintained when moving or rotating the group. Therefore, it is needless to move the respect object and adjust the relative position relation of the implant objects, and also only one manipulation make it possible to modify all the related objects simultaneously, which is very convenient.

Meanwhile, a device for the implant treatment planning according to another embodiment of the present invention can comprise a maximum convexity display unit 80.

The maximum convexity display unit 80 detects a maximum convexity of natural teeth or artificial teeth and displays a maximum convexity of each tooth in 2D or 3D image model. The maximum convexity display unit 80 according to the invention keeps and displays a maximum convexity of each tooth crown in a changed slice although the position of slice in 2D or 3D model are changed. Conventionally, if the position of slice changes, the most outer part of teeth in the slice used to be displayed and in this case, when determining the position of an implant object, it should be done to adjust the slice position, checking the image and the properness of the position of the implant objects, which is so inconvenient.

Figure 4:
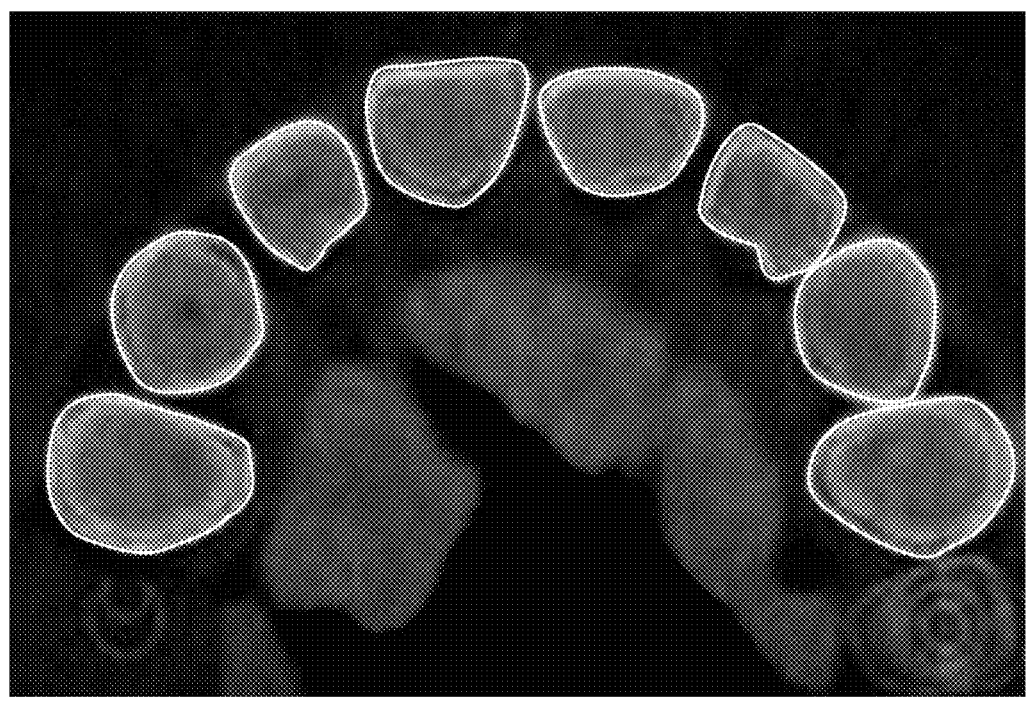
FIG. 4 illustrates an example of marking a maximum convexity of natural tooth crown or artificial tooth crown in the image model about patient's teeth arrangement, according to an embodiment of the present invention.

Otherwise, in the present invention, although the position of the slice is changed in 2D or 3D model, the maximum convexity of the tooth is displayed constantly. So, it is convenient that users can check intuitively whether the position is adjusted well or not, without checking or adjusting a position of a slice again. FIG. 4 illustrates an example of marking a maximum convexity of natural tooth crown or artificial tooth crown in the image model about patient's teeth arrangement, according to an embodiment of the present invention. Referring to FIG. 4, the maximum convexity of each tooth are marked with the yellow line, which is effective to determine a position or select an implant by displaying the maximum convexity of teeth constantly when planning an implant treatment.

For example, although users move the slice position of teeth model, not the most outer part of each tooth in the slice, but the maximum convexity of each tooth remains displayed, so users can check whether the position adjustment of the implant object is proper or not without changing the slice.

Figure 5:
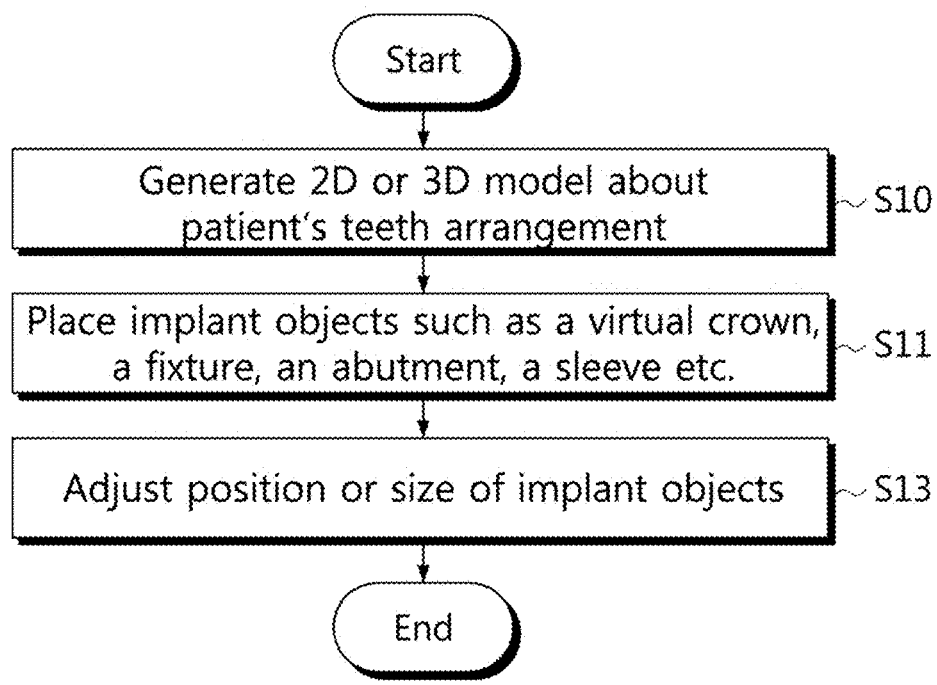
FIG. 5 is a flowchart for a method of the dental implant treatment planning according to an embodiment of the present invention.

Hereinafter, a method of the dental implant treatment planning according to another embodiment of the present invention will be described. FIG. 5 is a flowchart of a method of the dental implant treatment planning according to an embodiment of the present invention, and FIG. 6 is a flowchart of a method of position movement or rotation of an implant object.

Referring to FIG. 5, a method of the dental implant treatment planning according to another embodiment of the present invention generates an image model about patient's teeth arrangement such as 2D or 3D model in step S10, and generates and places in the model the implant objects (e.g. virtual crown, fixture, abutment, etc.) in step S11. A user plans the exact insertion position etc. by adjusting the position and size etc. or the implant object in step S13.

Figure 6:
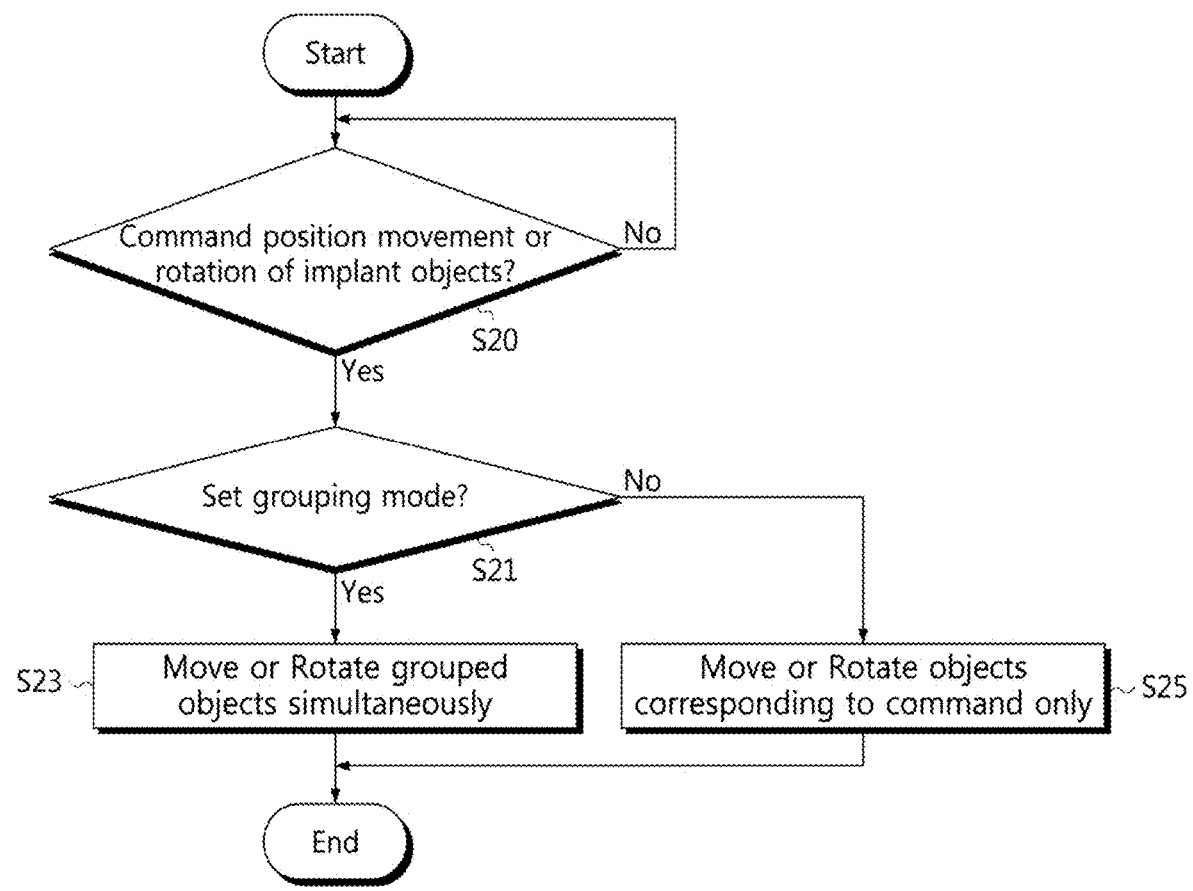
FIG. 6 is a flowchart of a method of position movement or rotation of an implant object.

Referring to FIG. 6, if the movement or rotation commands of the implant object are entered by a user in step S20, whether the implant objects are grouped or not is determined in step S21. If the implant objects are grouped, the grouped implant objects are moved or rotated simultaneously in step S23. At this moment, the grouped objects are moved or rotated in the state with relative position of the objects kept.

If they are not grouped, only the object corresponding to command is moved or rotated in step S25.

Figure 7:
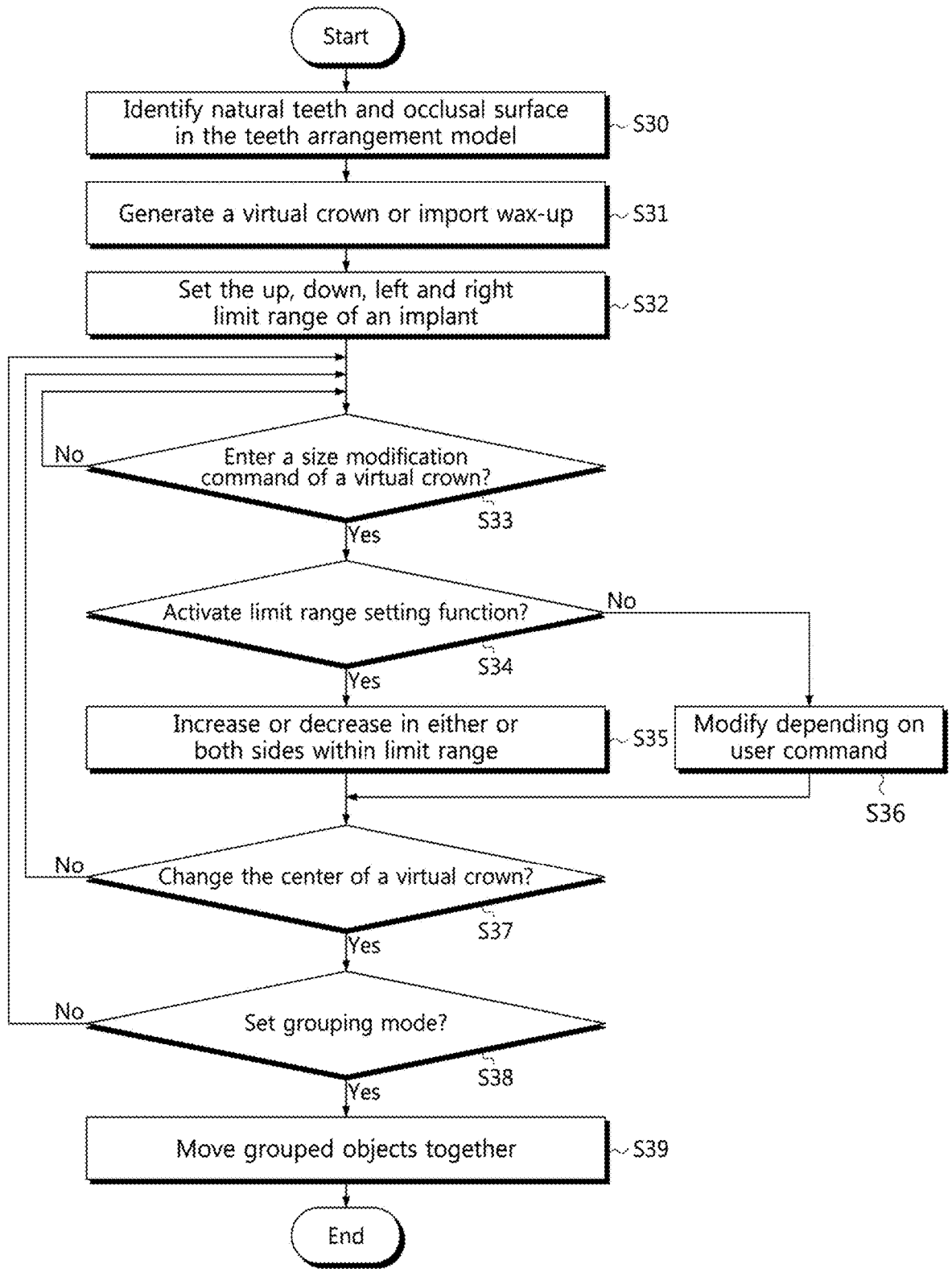
FIG. 7 is a flowchart of a method of modifying size of an implant object in the dental implant treatment planning according to another embodiment of the present invention.

FIG. 7 is a flowchart of a method of modifying size of an implant object in the dental implant treatment planning according to another embodiment of the present invention.

Referring to FIG. 7, natural teeth or occlusal surface are recognized in patient's teeth arrangement in step S30. And an implant object is generated according to user's selection or input or by the import of the Wax-up in step S31. Herein, the maximum convexity of each tooth crown can be displayed in the model of teeth arrangement. Although the position of axial slice is changed by user's selection, the maximum convexity of each tooth is displayed constantly. So, it is easy to check whether position determination is proper or not because a user can see the maximum convexity of each tooth intuitively although the slice position is moved.

Meanwhile, in step S32, the limit range of up, down, left and right for a virtual crown is set based on the identification result about natural teeth and occlusal surface corresponding to teeth arrangement. The limit range of the virtual crown is set by the position of maximum convexity, neural tube and alveolar bone of teeth adjacent to the virtual crown.

For example, alarm function can be provided to user which is activated when a virtual crown invades in the most outer part of the natural tooth. To prevent invading alveolar bone, the up or down movement more than predetermined value (e.g. 1 mm) from the alveolar bone can be restricted. Also, the down movement can be restricted when conflicting with neural tube.

For example, the up and down movement of a virtual crown is restricted based on identification results of occlusal surface, and the boundary surface of left and right movement of the implant virtual crown is considered as the boundary surface of maximum convexity of natural teeth, artificial teeth and virtual crown. In addition, by displaying such a boundary surface on the tooth model, the user can intuitively recognize the boundary surface with reference to the modification of the implant, which may increase the accuracy of the object positioning.

As stated above, the limit range setting function is set automatically, so it can be applied absolutely when moving, rotating or modifying implant objects, but it also can be activated or deactivated depending on user's selection.

If the above limit range setting function is activated or deactivated by user's selection, after calculating the data about the limit range—the up, down, left and right limits—when creating or placing an implant object, the function may be activated and deactivated later according as users select the limit range setting function or not. In the other examples, after users selecting the limit range setting function, then the function can be activated by calculating the limit range for implants. Thus, FIG. 7 illustrates to set the limit range in step S32, but it can be applied in various orders as needed, for example, In FIG. 7, the order of the steps S31 and S32 can be changed, or S32 can be done at the order between S34 and S35. Referring to FIG. 7 again, if a size modification command for a virtual crown is entered by users in step S33, then an implant modification unit 30 checks whether the limit range setting function is activated or not in step S34, and if the limit range setting function is activated, the virtual crown on either or both sides are increased or decreased within the range in step S35. Meanwhile, if the limit range setting function is deactivated, the size is increased or decreased on horizontal or vertical side or all sides according to command of user's interface unit users without restricting the limit range in step S36.

In step S37, whether the center of maximum convexity for the virtual crown has been moved or not by increasing or decreasing the virtual crown is determined, and if the center of the virtual crown has been moved and objects has been grouped in step S38, other grouped objects are moved together in step S39. However, if the center of the virtual crown has not been moved according to the size modification of the virtual crown, moving other objects is unnecessary.

Figure 8:
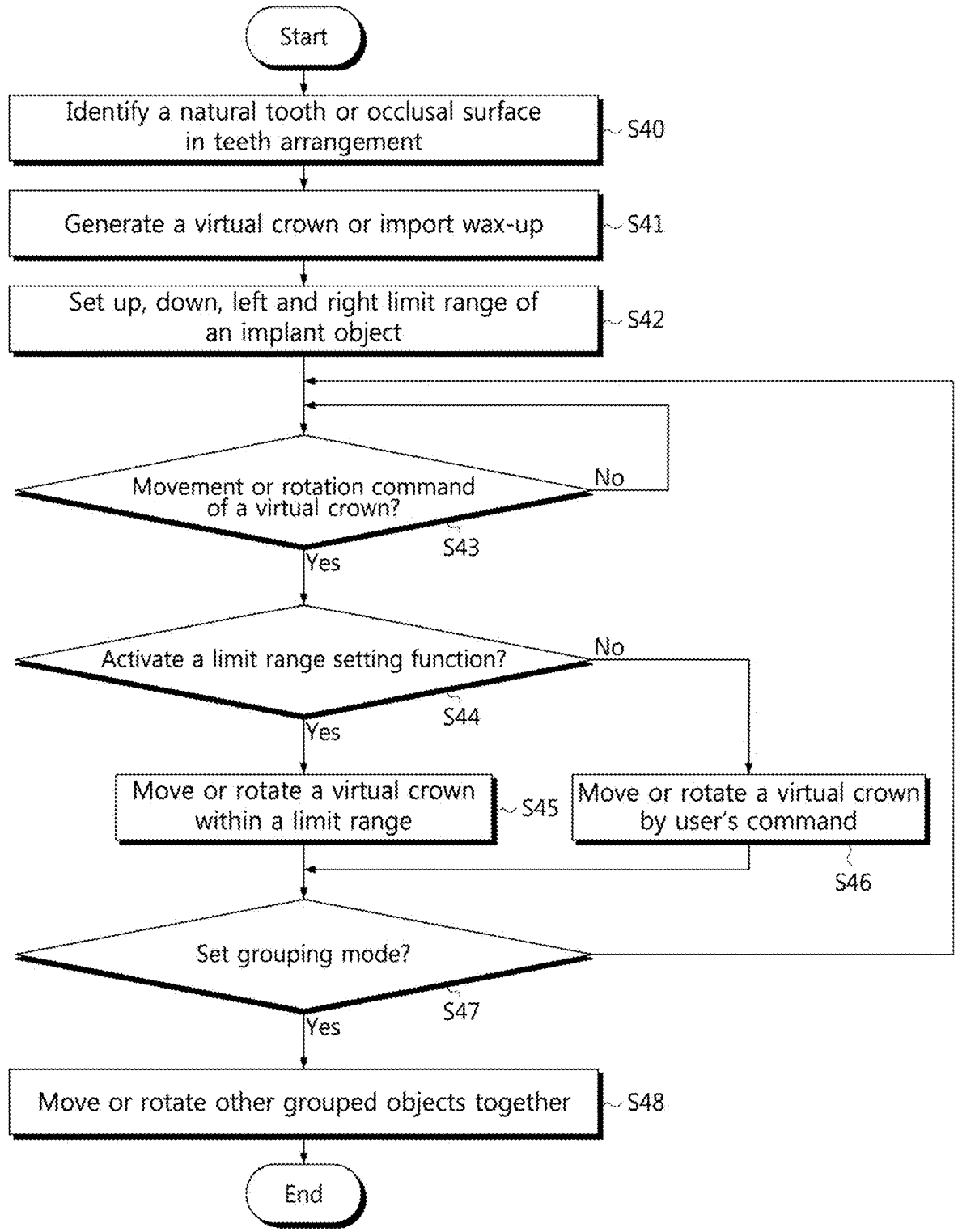
FIG. 8 is a flowchart of a method of position movement or rotation of an implant object in the dental implant treatment planning according to another embodiment of the present invention.

In FIG. 8 is a flowchart of a method of position movement or rotation of an implant object from the dental implant treatment planning according to another embodiment of the present invention. Overlapping description in the stated embodiment will be skipped for the clarity and simplicity of the explanation.

Referring to FIG. 8, it is done to identify the natural tooth or the occlusal surface in the teeth arrangement of a patient model in step S40. And it generates an object according to the user's selection or input, or import of the implant wax-up in step S41.

At this time, it sets the limit range of the movement up, down, left, and right of the implant object on the basis of the natural teeth or occlusal identification result in step S42. The limit range of the implant object is set based on the maximum convexity, neural tube, and the position of the bone of the adjacent teeth and the virtual crown.

For example, the up and down movement of a virtual crown is limited based on the identification results of occlusal surface, and the boundary surface of maximum convexity of a virtual crown is considered as a boundary surface of the left and right movement of a virtual crown. In addition, it increases accuracy of placing implant object because users can recognize the boundary surface intuitively by displaying such a boundary surface in teeth model.

If position modification commands of a virtual crown are entered by users in step S43, it checks whether a limit range setting function is activated or not in step S44. If the limit range setting function is activated, it is able to be moved or rotated within a limit range n in step S45, or if the limit range setting function is deactivated, it is able to be moved or rotated freely by user's command in step S46. When moving or rotating the virtual crown, if objects are grouped by checking whether they are grouped or not in step S47, it moves or rotates other grouped objects together in step S48. Otherwise, it modifies the virtual crown alone.

When a limit range setting function is activated, if user gives a command which the implant object is out of the up, down, left and right limit range, outputting message, icon, voice etc. leads to guide for determining the position of the implant within a limit range. Among embodiments of the stated present invention, the screen for teeth implant treatment planning in FIG. 2 and FIG. 3 illustrates as panorama image model, but it may represent four kinds of view—axial, coronal, sagittal, cross-sectional by 3D model, and when modifying an object in one of the screens, it can be implemented applying the modification immediately in other view as well.

The device for dental implant treatment planning of the invention can be implemented as a device having at least one programmable processor combined with memory device including at least one memory type such as RAM, ROM etc.

The processor can be used for general or specific uses, the device and method for the dental implant treatment planning according to an embodiment of the present is implemented by digital electrical circuit, computer hardware, firmware, software or those combinations. Also, the device can be implemented as a computer program providing the method for implant treatment planning according to the invention when it runs on the computer. The computer program is implemented as storage medium containing a computer-readable code to be run by programmable processor. Therefore, the invention is implemented as a computer-readable storage medium containing the computer program that gives command to run the same method for the implant treatment planning as stated when it runs on computer.

The above description has been made only to the spirit of the invention described by way of example, those of ordinary skill in the art that various modifications, additions and substitutions will be possible without departing from essential characteristics of the invention. Thus, embodiments described herein are for illustrating but not for limiting the technical scope of the present invention, by such an embodiment is not limited the scope of the technical idea of the present invention. And scope of the invention should be construed by the following claims, and that all spirits within a scope equivalent will be construed as being included in the scope of the invention.

The above description has been made only to the spirit of the invention described by way of example, those of ordinary skill in the art that various modifications, additions and substitutions will be possible without departing from essential characteristics of the invention. Thus, embodiments described herein are for illustrating but not for limiting the technical scope of the present invention, by such an embodiment is not limited the scope of the technical idea of the present invention. And scope of the invention should be construed by the following claims, and that all spirits within a scope equivalent will be construed as being included in the scope of the invention.

What is claimed is:

1. A method of modeling a dental implant design by a processor, the method comprising:
   generating a multi-dimensional image model corresponding to a teeth arrangement of a patient;
   placing, in the image model, multiple objects that form a dental implant;
   activating or deactivating a grouping function according to a user's selection;
   upon activation of the grouping function, grouping two or more of the multiple objects; and
   moving or rotating, relative to the teeth arrangement, the grouped multiple objects together so that relative position relationship of the grouped multiple objects is maintained when one of the grouped multiple objects is moved or rotated;
   wherein the grouped multiple objects include a virtual crown and a fixture, and
   wherein, when the virtual crown is moved or rotated, the virtual crown and the fixture are configured to move or rotate simultaneously about a center axis of the virtual crown, and when the fixture is moved or rotated, only the fixture is configured to independently move or rotate while the virtual crown remains its position,
   the method further comprising:
   identifying natural or artificial teeth and one or more occlusal surfaces in the teeth arrangement;
   setting limit ranges where the multiple objects can be placed; and
   detecting a maximum convexity of each tooth of the natural or artificial teeth and displaying the maximum convexity of each tooth in the image model,
   wherein an execution of a command for position movement, rotation, or size modification of the multiple objects is made within the limit ranges,
   wherein a size of the virtual crown is restricted to be increased by alarming not to go over a boundary surface of a maximum convexity of a tooth which is adjacent to the virtual crown when the size of the virtual crown is modified, upon activation of a limitation setting function, and wherein the maximum convexity of each tooth of the natural or artificial teeth is constantly displayed, even when a slice of the image model is changed.

2. The method of claim 1, further comprising:

moving a position of the fixture along with the virtual crown if a center of the virtual crown changes according to the size modification of the virtual crown when modifying a size of the virtual crown.

3. The method of claim 1, wherein the limit ranges are set based on at least one among positions of the maximum convexity, a neural tube and an alveolar bone of the tooth which is adjacent to the virtual crown.

4. The method of claim 1, wherein the setting of the limit ranges comprises restricting up and down movements of the virtual crown by identifying the one or more occlusal surfaces.

5. The method of claim 1, further comprising:

marking the maximum convexity of each tooth of the natural or artificial teeth in the image model.

6. A non-transitory tangible computer-readable recording medium to record a program for the execution of the method of claim 1.

7. A device for modeling a dental implant design, the device comprising a processor configured for:

generating a multi-dimensional image model corresponding to a teeth arrangement of a patient;

grouping two or more of multiple objects that form a dental implant placed in the image model, upon activation of a grouping function according to a user's selection; and moving or rotating, relative to the teeth arrangement, the grouped multiple objects together so that relative position relationship of the grouped multiple objects is maintained when one of the grouped objects is moved or rotated, wherein the grouped multiple objects include a virtual crown and a fixture, and wherein, when the virtual crown is moved or rotated, the virtual crown and the fixture are configured to move or rotate simultaneously about a center axis of the virtual crown, and when the fixture is moved or rotated, only the fixture is configured to independently move or rotate while the virtual crown remains its position, the processor being further configured for:

identifying natural or artificial teeth and one or more occlusal surfaces in the teeth arrangement;

setting limit ranges where the multiple objects can be placed; and detecting a maximum convexity of each tooth of the natural or artificial teeth and displaying the maximum convexity of each tooth in the image model, wherein an execution of a command for position movement, rotation, or size modification of the multiple objects is made within the limit ranges, wherein a size of the virtual crown is restricted to be increased by alarming not to go over a boundary surface of a maximum convexity of a tooth which is adjacent to the virtual crown when the size of the virtual crown is modified, upon activation of a limitation setting function, and wherein the maximum convexity of each tooth of the natural or artificial teeth is constantly displayed, even when a slice of the image model is changed.

8. The device of claim 7, wherein the processor is further configured to move a position of the fixture along with the virtual crown, if the virtual crown and the fixture are grouped and a center of the virtual crown changes due to the size modification of the virtual crown.

9. The device of claim 7, wherein the processor is further configured for outputting at least one signal among a message, voice or vibration, if a range of the position movement or the rotation of the multiple objects is out of the limit ranges.

10. The device of claim 7, wherein the processor is further configured for:

storing the multiple objects that form the dental implant, and arranging the multiple objects in the image model corresponding to the teeth arrangement by generating at least one of the multiple objects or importing a wax-up result from an implant library.

11. The device of claim 7, wherein the processor is configured to detect the maximum convexity of each tooth of the natural or artificial teeth by analyzing an image of the teeth arrangement.

* * * * *